United States Patent [19]

Lampadius

[11] Patent Number: 4,721,110

[45] Date of Patent: Jan. 26, 1988

[54] RESPIRATION-CONTROLLED CARDIAC PACEMAKER

[76] Inventor: Michael S. Lampadius, Rothenberg Süd 18, D-8113 Kochel am See, Fed. Rep. of Germany

[21] Appl. No.: 758,481

[22] Filed: Jul. 24, 1985

[30] Foreign Application Priority Data

Aug. 6, 1984 [DE] Fed. Rep. of Germany ....... 3428975

[51] Int. Cl.$^4$ .............................................. A61N 1/36
[52] U.S. Cl. ............................................. 128/419 PG
[58] Field of Search .......................... 128/419 PG, 625

[56] References Cited

U.S. PATENT DOCUMENTS 3,593,718  7/1971  Krasner et al. .............. 128/419 PG
4,567,892  2/1986  Plicchi et al. ................ 128/419 PG

FOREIGN PATENT DOCUMENTS 0089014  9/1983  European Pat. Off. .
151689   8/1985  European Pat. Off. ..... 128/419 PG
3243094  5/1983  Fed. Rep. of Germany .

*Primary Examiner*—William E. Kamm
*Attorney, Agent, or Firm*—Toren, McGeady & Associates

[57] ABSTRACT

The respiration-controlled cardiac pacemaker includes a stimulation pulse generator (3) generating stimulating pulses at a controllable basic stimulation rate, a rheography pulse generator (17) producing rheography pulses of constant amplitude and a respiration detector (21) which, as a function of the impedance data of the rheography pulses, generates a respiration signal representing the respiratory rate and/or the depth of respiration. Control device (11) control the basic stimulation rate of the stimulation pulse generator (3) in accordance with a predetermined respiration signal—basic stimulation rate—characteristic as a function of the respiration signal. The rheography pulse generator (17) generates the rheography pulses to a timing dependent upon the stimulating pulses and/or inhibiting pulses, preferably within the refractory time intervals in each case associated with the individual stimulating pulses or inhibiting pulses and in which the stimulation pulse generator is blocked. It is convenient that the rheography pulses are generated within the refractory time intervals preceding the individual stimulating pulses. Associated with each stimulting pulse or inhibiting pulse is a single rheography pulse. In this way, stimulation upsets and disturbances of the ECG by the rheography pulses are avoided and in the event of hyperventilation, any undesired rise in basic stimulation rate is avoided.

12 Claims, 9 Drawing Figures

RESPIRATION-CONTROLLED CARDIAC PACEMAKER

BACKGROUND OF THE INVENTION

The invention relates to a respiration-controlled cardiac pacemaker.

A cardiac pacemaker is known from published European Patent Specification No. 89 014, the basic stimulating pulse rate of which is controlled as a function of respiration, in order to be able to adapt the stimulation rate more appropriately to the physiological needs of the patient. A rheography pulse generator of the pacemaker generates, at a constant frequency, successive constant current pulses which flow between two electrodes implanted at a distance from each other in the ribcage of a patient. The voltage between the two electrodes is proportional to the ribcage impedance and varies as a function of respiration as the ribcage expands. A respiration detector, responding to the voltage amplitude of the rheography pulses, provides, for instance by time-related integration of the pulse-voltage amplitudes, a respiration signal which corresponds to the voltage fluctuation and hence the rate of respiration. Control means control the basic stimulation rate of the cardiac pacemaker as a function of the respiration signal in accordance with a predetermined respiration signal—basic stimulation rate characteristic, particularly in that the basic stimulation rate is raised with increasing respiration rate.

In the case of the known cardiac pacemaker, the frequency of the rheography pulses is considerably greater than the basic stimulation rate. This can lead to stimulation disturbances, because the cardiac pacemaker is, in certain circumstances, inhibited by its own rheography pulses. Furthermore, ECG measurements are made more difficult because the rheography pulses appear in the ECG picture and make it difficult to monitor the cardiac pacemaker function on the patient. Furthermore, under conditions of hyperventilation which are linked with a sudden increase in respiration rate, the increase in basic stimulation rate which is undesirable in such a case cannot be prevented.

The object of the invention is to improve a respiration-controlled cardiac pacemaker of the previously described type so that disturbances of the ECG picture caused by rheography pulses are kept within negligible limits.

SUMMARY OF THE INVENTION

According to the invention, the rheography pulse generator generates the rheography pulses to a timing dependent upon the stimulating pulses and/or inhibiting pulses, which block the stimulating pulse generator from emitting stimulating pulses. Thus, the rheography pulses enjoy, in terms of timing, a fixed relationship with the cardiac action potentials recorded by the ECG recorder and can be clearly separated from the natural rhythm potentials of the patient as well as from the stimulation potentials. Such a rheography pulse generator can be used with any type of cardiac pacemaker so long as the basic stimulation rate of the stimulating pulse generator is controllable as a function of respiration. The demand type of cardiac pacemaker is certainly preferred. Now and henceforth, the term 'basic stimulation rate' is to be understood as meaning the rate at which the stimulating pulses follow one another or would follow one another were they not suppressed by inhibiting pulses.

Usually associated with the stimulating pulses and/or inhibiting pulses is a refractory time interval during which the cardiac pacemaker is 'blind' and can respond neither to intracardial signals of the patient nor to his stimulation reply. In a preferred embodiment, the rheography pulse generator generates the rheography pulses within these refractory time intervals. In this way, any disturbance of the cardiac pacemaker operation and any incorrect stimulation of the patient by the rheography pulses can be reliably prevented.

Preferably, the refractory time interval of the stimulation pulses starts shortly before the stimulating pulse. It has been found expedient for the rheography pulse generator to generate the rheography pulses within a refractory time interval which, in each case, immediately precedes the individual stimulating pulses. Consequently, the stimulating pulse or polarization phenomena cannot affect rheography measurement by reason of this pulse.

Preferably, the rheography pulse generator generates a single rheography pulse for each stimulating pulse and/or inhibiting pulse. This simple dimensioning rule means that the problem, referred to at the outset, of an undesired increase in basic stimulation rate in the event of sudden hyperventilation is overcome. The scanning frequency, determined by the rate of succession of rheography pulses and at which variations in impedance and thus fluctuations in respiration are detected, is so low that the respiration detector cannot follow considerable fluctuations in respiratory rate such as occur in hyperventilation.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

DETAILED DESCRIPTION OF THE DRAWINGS

Figure 1:
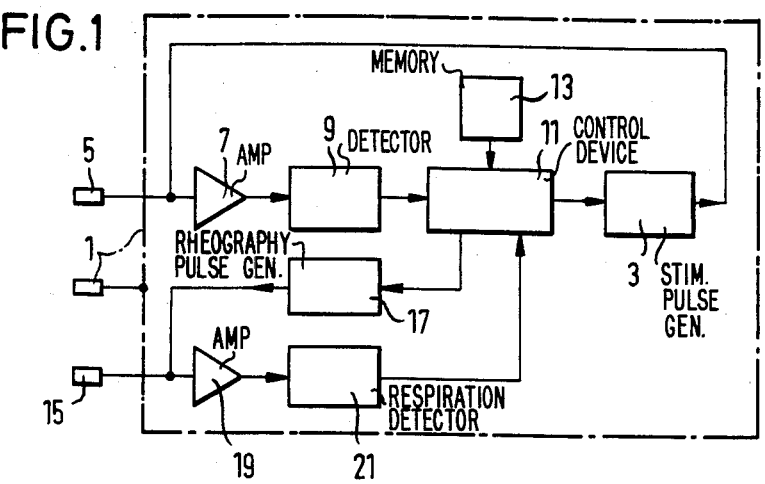
FIG. 1 is a block circuit diagram of a respiration-controlled pacemaker of the demand type.

The implantable cardiac pacemaker shown in FIG. 1 contains, in a housing 1, which at the same time forms a neutral electrode, a stimulation pulse generator 3 which emits stimulating pulses at a controllable basic stimulation rate via a stimulating electrode 5 which is implanted in a patient's heart. A detector 9, likewise connected to the stimulating electrode 5 via an amplifier 7, responds to the cardiac action potential of the patient's own body, for instance the R- or P-wave, and when this cardiac action potential occurs at its input, it generates, in each case, an inhibiting pulse which, through a control device, blocks the stimulation pulse generator 3 from emitting a stimulating pulse. The control device 11 determines the basic stimulation rate of the stimulation pulse generator 3. In order to be able to adapt the basic stimulation rate to the physiological needs of the patient, the basic stimulation rate can, as a function of the respiratory rate and/or as a function of the depth of respiration, be controlled according to a respiration stimulation rate characteristic predetermined by a memory 13 or a function generator or the like. The respiratory rate is ascertained by measuring the patient's ribcage impedance. To this end, there is subcutaneously implanted into the ribcage, at a distance from the neutral electrode 1, a rheography electrode 15 to which a rheography pulse generator 17 feeds constant current pulses of constant current amplitude. Depending upon the impulse voltage values present between the electrodes 1 and 15 during the rheography pulses, a respiration detector 21, connected to the rheography electrode 15 via an amplifier 19, generates a signal which corresponds to the frequency of the voltage fluctuation and, therefore, to the respiratory rate. This respiration signal is fed to the control device 11 which, as a function of the respiration signal, controls the basic stimulation rate according to the given respiration—basic stimulation rate—characteristic.

The respiration detector 21 can be conventionally constructed and the fluctuation rate at which the voltage amplitudes of the rheography pulses fluctuate as a function of respiration can be ascertained therein by integration or by means of a digital computer.

The control device 11 triggers the rheography pulse generator 17 to emit a single rheography pulse for each inhibiting pulse and each stimulating pulse and in close proximity, in terms of time. In this way, stimulation disturbances can be avoided.

Figure 2A:
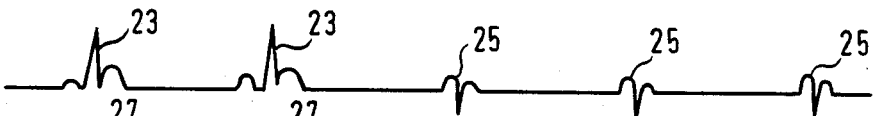
FIGS. 2a to 2d are time diagrams with cardiac action potentials, inhibiting pulses, stimulating pulses and rheography pulses.
Figure 2B:
Figure 2C:
Figure 2D:

FIG. 2a shows the cardiac action potential of the patient. Reference numeral 23 denotes the autonomous QRS complex. Reference numeral 25 denotes cardiac action potentials which arise as a result of the stimulating pulse of the cardiac pacemaker. FIG. 2b shows, at 27, the inhibiting pulses generated by the detector 9 when the autonomous QRS complex 23 occurs. Each of the inhibiting pulses 27 is immediately followed by a refractory time interval 29 in which the cardiac pacemaker is 'blind' to further pulses occurring at its stimulating electrode 5. The inhibiting pulses 27, as shown in FIG. 2c, block the stimulation pulse generator 3 and prevent the emission of stimulating pulses. If no autonomous cardiac action potentials occur within a time interval determined by the basic stimulation rate, and hence no inhibiting pulses, the stimulation pulse generator 3 emits stimulating pulses 31. Each of the stimulating pulses 31 is preceded directly by a refractory time 33 and is immediately followed by a refractory time 35. Within these refractory times, the cardiac pacemaker is likewise 'blind' and cannot be inhibited by pulses at its stimulation electrode 5. FIG. 2d shows the rheography pulses 37 triggered by the control means 11. When inhibiting pulses 27 arise, the rheography pulses 37 are triggered during the inhibiting pulse 27 or during the subsequent refractory time 29. If there are no inhibiting pulses, the rheography pulses 37 are generated during the refractory time 33 preceding each stimulating pulse 31. It is possible, in this way, to ensure that rheography measurement is not upset by stimulating pulses or by polarization phenomena triggered by these pulses.

Figure 3A:
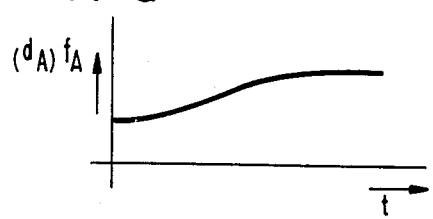
FIGS. 3a and 3b are related time diagrams of respiratory rate and basic stimulation rate with a slow variation in respiratory rate.
Figure 4A:
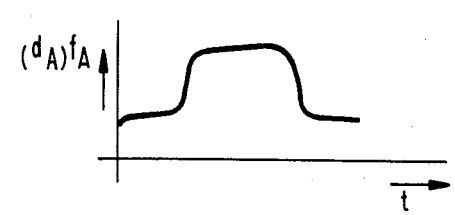
FIGS. 4a and 4b are related time diagrams of respiratory rate and stimulation rate with a rapid variation in respiratory rate.
Figure 3B:
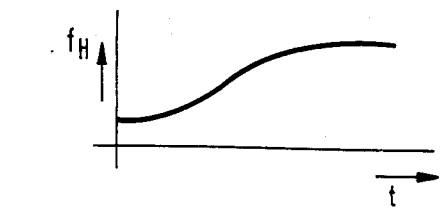
Figure 4B:
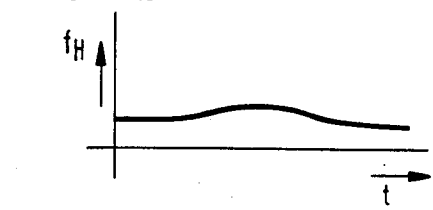

FIGS. 3a and 3b show, in correlated time diagrams, the respiratory rate $f_A$ and the basic stimulation rate $f_H$ in each case as a function of the time t. The respiratory rate $f_A$ varies only slowly and correspondingly, too, the basic stimulation rate $f_H$ varies slowly. FIGS. 4a and 4b show, in mutually associated time diagrams, the respiratory rate $f_A$ and the basic stimulation rate $f_H$ for a rapid variation in respiratory rate such as occurs, for example, during hyperventilation. During this often only brief rapid rise in respiratory rate, not caused by physical strain or the like, the basic stimulation rate should not change, or should only do so negligibly, as shown in FIG. 4b. The characteristic curve in FIG. 4b is, in the case of the pacemaker shown in FIG. 1, achieved in that only a single rheography pulse is generated in each period of the basic stimulation rate. In consequence, for evaluating voltage fluctuations of rheography pulses, the only voltage values available follow one another at a relatively low scanning frequency. Rapid voltage fluctuations such as might occur in the case in FIG. 4a, do not lead therefore to a change of output signal from the respiratory detector 21, so that the basic stimulation rate is not altered either.

The relationship of the depth of respiration $d_A$ to the stimulation frequency $f_H$ is, in principle, the same as that for rate of respiration $f_A$ to the stimulation frequency. Hence, the y-axis of FIGS. 3a and 4a are alternately identifed as $d_A$.

While specific embodiments of the invention have been shown and described in detail to illustrate the application of the inventive principles, it will be understood that the invention may be embodied otherwise without departing from such principles.

I claim:

1. A respiration-controlled cardiac pacemaker comprising:

a stimulating pulse generator for generating stimulating pulses at a controllable basic stimulation rate;

a rheography pulse generator for generating rheography pulses in synchronism and at a predetermined timed interrelationship with said stimulating pulses;

a respiration detector responsive to said rheography pulses and generating a respiration signal indicative of a patent's respiration rate;

means for providing a predetermined respiration signal-basic stimulation rate-characteristic; and control means for controlling said basic stimulation rate of said stimulating pulse generator according to said predetermined respiration signal—basic stimulation rate—characteristic in response to said repiration signal.

2. Cardiac pacemaker according to claim 1, wherein said control means comprises means for causing said rheography pulse generator to generate a single rheography pulse for each stimulating pulse.

3. A respiration-controlled cardiac pacemaker comprising:

a stimulating pulse generator for generating stimulating pulses at a controllable basic stimulation rate;

means for detecting cardiac action potential and for generating, each time, an inhibiting pulse;

a rheography pulse generator for generating rheography pulses;

a respiration detector responsive to said rheography pulses for generating a respiration signal indicative of a patient's respiration rate;

means for supplying a predetermined respiration signal-basic stimulation rate-characteristic; and control means for controlling the basic stimulation rate of said stimulating pulse generator according to said predetermined respiration signal-basic stimulation rate-characteristic in response to said respiration signal, said control means stopping said stimulating pulse generator from generating a stimulating pulse in response to each inhibiting pulse, and for causing said rheography pulse generator to generate said rheography pulses in synchronism and at a predetermined timed interrelationship with said stimulating pulses and said inhibiting pulses.

4. Cardiac pacemaker according to claim 3, wherein said control means comprises means for blocking said stimulating pulse generator from generating pulses within a first predetermined refractory time interval associated with each of said inhibiting pulses, and means for causing said rheography pulse generator to generate said rheography pulses within said first predetermined refractory time interval and within a second predetermined refractory time interval associated with each of said stimulating pulses.

5. Cardiac pacemaker according to claim 4, wherein said second predetermined refractory time interval, in each case, immediately precedes each of said stimulating pulses.

6. Cardiac pacemaker according to claim 3, wherein said control means comprises means for causing said rheography pulse generator to generate a single rheography pulse for each stimulating pulse.

7. A respiration-controlled cardiac pacemaker comprising:
a stimulating pulse generator for generating stimulating pulses at a controllable basic stimulation rate;
a rheography pulse generator for generating rheography pulses in synchronism and at a predetermined timed interrelationship with said stimulating pulses;
a respiration detector responsive to said rheography pulses and generating a respiration signal indicative of a patent's depth of respiration;
means for providing a predetermined respiration signal-basic stimulation rate-characteristic; and
control means for controlling said basic stimulation rate of said stimulating pulse generator according to said predetermined respiration signal—basic stimulation rate—characteristic in response to said repiration signal.

8. Cardiac pacemaker according to claim 7, wherein said control means comprises means for causing said rheography pulse generator to generate a single rheography pulse for each stimulating pulse.

9. A respiration-controlled cardiac pacemaker comprising:
a stimulating pulse generator for generating stimulating pulses at a controllable basic stimulation rate;
means for detecting cardiac action potential and for generating, each time, an inhibiting pulse;
a rheography pulse generator for generating rheography pulses;
a respiration detector responsive to said rheography pulses for generating a respiration signal indicative of a patient's depth of respiration;
means for supplying a predetermined respiration signal-basic stimulation rate-characteristic; and
control means for controlling the basic stimulation rate of said stimulating pulse generator according to said predetermined respiration signal-basic stimulation rate-characteristic in response to said respiration signal, said control means stopping said stimulating pulse generator from generating a stimulating pulse in response to each inhibiting pulse, and for causing said rheography pulse generator to generate said rheography pulses in synchronism and at a predetermined timed interrelationship with said stimulating pulses and said inhibiting pulses.

10. Cardiac pacemaker according to claim 9, wherein said control means comprises means for blocking said stimulating pulse generator from generating pulses within a first predetermined refractory time interval associated with each of said inhibiting pulses, and means for causing said rheography pulse generator to generate said rheography pulses within said first predetermined refractory time interval and within a second predetermined refractory time interval associated with each of said stimulating pulses.

11. Cardiac pacemaker according to claim 10, wherein said second predetermined refractory time interval, in each case, immediately precedes each of said stimulating pulses.

12. Cardiac pacemaker according to claim 9, wherein said control means comprises means for causing said rheography pulse generator to generate a single rheography pulse for each stimulating pulse.

* * * * *